US010524741B2

(12) United States Patent
Florent et al.

(10) Patent No.: US 10,524,741 B2
(45) Date of Patent: Jan. 7, 2020

(54) AUTOMATED IDENTIFICATION OF AN ANATOMY PART

(75) Inventors: Raoul Florent, Ville d'Avray (FR); Willem Frederik Den Hartog, Eindhoven (NL); Vincent Maurice Andre Auvray, Paris (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1166 days.

(21) Appl. No.: 13/637,373

(22) PCT Filed: Mar. 24, 2011

(86) PCT No.: PCT/IB2011/051262
§ 371 (c)(1),
(2), (4) Date: Sep. 26, 2012

(87) PCT Pub. No.: WO2011/121504
PCT Pub. Date: Oct. 6, 2011

(65) Prior Publication Data
US 2013/0023759 A1 Jan. 24, 2013

(30) Foreign Application Priority Data
Mar. 31, 2010 (EP) .................................. 10305333

(51) Int. Cl.
*A61B 5/05* (2006.01)
*A61B 6/12* (2006.01)

(52) U.S. Cl.
CPC ..................................... *A61B 6/12* (2013.01)

(58) Field of Classification Search
USPC ...................................................... 600/424
See application file for complete search history.

(56) References Cited

U.S. PATENT DOCUMENTS

| 5,476,453 A | 12/1995 | Mehta |
| 6,341,152 B1 | 1/2002 | Sugihara |
| (Continued) | | |

FOREIGN PATENT DOCUMENTS

| CN | 101342082 | 1/2009 |
| DE | 10325003 | 12/2004 |
| (Continued) | | |

OTHER PUBLICATIONS

M.G. Bourassa et al., "Selective Coronary Arteriography by the Percutaneous Femoral Artery Approach", From the Montreal Heart Institute, Montreal, Quebec, Canada, vol. 107, No. 2, pp. 377-383.
(Continued)

*Primary Examiner* — Jonathan Cwern

(57) ABSTRACT

The present invention relates to a device 10 for automatically identifying a part 20a, 20b of an anatomy structure comprising several parts 20a, 20b, in which anatomy structure an intervention device 21 resides. The device 10 comprises a feature extraction unit 11 and an anatomy part classification unit 13. The feature extraction unit 11 uses provided image content data ICD to extract at least one characterizing feature DS of the appearance of 10 the intervention device 21. The anatomy part classification unit 13 correlates the at least one characterizing feature DS with provided classifier data CD which are characteristic for a projection feature of the intervention device 21 viewed under certain geometry of an imaging system 30. After correlating, the anatomy part classification unit 13 determines in which part 20a, 20b of the anatomy structure comprising several parts 20a, 20b the intervention device 2115 is located.

26 Claims, 6 Drawing Sheets

(56) References Cited

U.S. PATENT DOCUMENTS

| | | |
|---|---|---|
| 6,463,121 B1 | 10/2002 | Milnes |
| 6,898,302 B1* | 5/2005 | Brummer .................... 382/131 |
| 7,203,350 B2 | 4/2007 | Leichter |
| 8,608,481 B2* | 12/2013 | Simon ........................ 434/262 |
| 2004/0179010 A1* | 9/2004 | Wittenbrink et al. ........ 345/440 |
| 2005/0147303 A1 | 7/2005 | Zhou et al. |
| 2005/0272992 A1 | 12/2005 | O'Donnell et al. |
| 2006/0039600 A1* | 2/2006 | Solem et al. ................ 382/154 |
| 2006/0050941 A1 | 3/2006 | Middleton et al. |
| 2008/0200927 A1* | 8/2008 | Hartmann et al. ........... 606/130 |
| 2009/0208078 A1 | 8/2009 | Fritz et al. |
| 2009/0262980 A1* | 10/2009 | Markowitz et al. .......... 382/103 |
| 2009/0264752 A1* | 10/2009 | Markowitz et al. .......... 600/425 |
| 2010/0157041 A1* | 6/2010 | Klaiman et al. ................ 348/77 |
| 2010/0168562 A1* | 7/2010 | Zhao et al. .................. 600/426 |
| 2012/0123239 A1 | 5/2012 | Han |
| 2013/0165945 A9* | 6/2013 | Roelle et al. ................. 606/130 |
| 2016/0000324 A1 | 1/2016 | Rege |

FOREIGN PATENT DOCUMENTS

| | | |
|---|---|---|
| GB | 2457577 | 8/2009 |
| JP | H08280657 A | 10/1996 |
| JP | 2007513649 A | 5/2007 |
| JP | 2009254793 A | 11/2009 |
| WO | 2004012152 A2 | 2/2004 |
| WO | WO2005052860 | 6/2005 |
| WO | 2006003576 A2 | 1/2006 |
| WO | WO2009019649 | 2/2009 |
| WO | WO2009077915 | 6/2009 |
| WO | WO2009081297 | 7/2009 |
| WO | WO2009087821 | 7/2009 |

OTHER PUBLICATIONS

Bredno et al: "Algorithmic Solutions for Live Device-to-Vessel Match"; In Proceedings of SPIE—vol. 5370—Medical Imaging 2004:Image Processing, May 2004, pp. 1486-1497.

* cited by examiner

AUTOMATED IDENTIFICATION OF AN ANATOMY PART

FIELD OF THE INVENTION

The invention relates to imaging systems which inter alia can be used for percutaneous transluminal coronary angioplasty (PCTA). In particular, the invention relates to a device and method for automatically identifying a part of an anatomy structure comprising several parts, in which anatomy structure the intervention device resides.

BACKGROUND OF THE INVENTION

In an imaging system for percutaneous transluminal coronary angioplasty (PTCA) in catheter laboratories, for example for treatment of cardiac stenoses, a catheter is inserted into the vascular system at an access site. During the intervention, a flexible, partially or fully radio-opaque guidewire is advanced to the affected vascular structures (e.g. stenoses in coronaries, neurovascular aneurisms, or arteria-venous malformations). Fluoroscopic low-dose x-ray surveillance visualizes the guidewire and allows for the hand-eye-coordination of the interventionalist while advancing the guidewire. When positioned, the guidewire serves as rail to deliver interventional devices (e.g. balloons for dilation and stent delivery, detachable coils for aneurysm clotting). The delivery and deployment of the interventional devices is also fluoroscopy-controlled. US 2009/0208078 describes automatically associating coronary arteries with regions of the myocardium to which the arteries supply blood. The method uses three dimensional image data of a patient, and an axial image slice is used to identify candidate locations of the aorta.

SUMMARY OF THE INVENTION

Some system angulations of an imaging system are suited to visualize different anatomy parts at the same time. E.g. some system angulations are indeed suited to visualize both the left and right coronary trees. In a case where X-rays are used as radiation for imaging the different anatomy parts, similarly, in order to reduce the radiation dose, shutters or wedges can be used to filter out the X-rays corresponding to certain parts of the image. In order to avoid any unnecessary manipulation, default shutter/wedge positions can be determined from the system geometry. For this automatic default shutter/wedge positioning it is necessary to know which anatomy part is being treated, e.g. the left or right coronary tree.

In imaging systems for PTCA the information whether the right or the left coronary tree, i.e. the anatomy part, is treated, can be entered manually. However, this manual input is receptive for wrong inputs. The consequences of respective wrong inputs are that it is not possible to automatically use geometry adapted shutter/wedge positioning and that the shutter/wedge positions are wrongly chosen since they are chosen on the wrong assumption.

It would be advantageous to achieve an automated and reliable shutter/wedge positioning e.g. for use in an imaging system for PTCA without requesting user information.

The object of the present invention is solved by the subject-matter of the independent claims, wherein further embodiments are incorporated in the dependent claims.

It should be noted that the following described aspects of the invention apply also for the method, the program element, the computer readable medium, the device and the medical imaging system.

To better address one or more of theses concerns, in a first aspect of the invention there is provided a device for automatically identifying a part of an anatomy structure comprising several parts, in which anatomy structure an intervention device resides. The device comprises a feature extraction unit and an anatomy part classification unit. The feature extraction unit uses provided image content data ICD to extract at least one characterizing feature DS of the appearance of the intervention device. The anatomy part classification unit correlates the at least one characterizing feature DS with provided classifier data CD which are characteristic for a projection feature of the intervention device viewed under certain geometry of an imaging system. After correlating, the anatomy part classification unit determines in which part of the anatomy structure comprising several parts the intervention device is located. A reason why the anatomy part is indirectly identified through the appearance of the interventional device lying in this anatomy part comes from the fact that the anatomy is very weakly visible in the considered data (because for instance seen in X-ray), whereas the interventional device stands out much more clearly (because for instance it is very radio-opaque to X-rays).

According to another aspect of the invention the device further comprises a characterisation unit. The characterisation unit uses provided three dimensional data 3DD of a model of the intervention device which is located in a part of the several parts of the anatomy structure and uses provided system geometry data SGD of an imaging system to provide the classifier data CD.

According to yet another aspect of the invention the device further comprises an estimation unit. The estimation unit uses provided system geometry data SGD and provided three dimensional data 3DD of a model of the intervention device being located in a part of the several part of the anatomy structure to estimate a projection characteristics PS of the intervention device being located in a part of the several part of the anatomy structure. The feature extraction unit uses the estimated projection feature PS of the device to extract the characterizing feature DS of the intervention device.

According to another aspect of the present invention a method for automatically identifying a part of an anatomy structure comprising several parts, in which anatomy structure an intervention device resides comprises a step of deriving at least one parameter from the extracted characterizing feature DS of the intervention device located in a part of the several parts of the anatomy structure, wherein the classifier data CD is at least one classifier parameter CP characteristic for a projection feature of the intervention device located in a part of the several parts of the anatomy structure. In the step of correlating, the at least one parameter is correlated with the at least one classifier parameter CP.

In order to determine the anatomy part in which an intervention device resides, e.g. the intervention side, the invention proposes to rely on the presence of an intervention or treatment device in the structure of interest which e.g. might be the vessels. The device's shape or other characteristics like its radio-opaqueness are analyzed and the corresponding features are extracted. Based on a formal description (model) of the intervention device and of the surrounding anatomy and based on the current system geometry (viewing angle, field of view), the anatomy part classification unit can determine in which anatomy part, such as the intervention side, the intervention device resides from the entered features. More generally speaking, the anatomy part classification unit can indirectly identify a non-visible anatomy part from the image data (here the projection) of a visible intervention device residing in this anatomy part.

These and other aspects of the present invention will become apparent from and elucidated with reference to the embodiments described hereinafter.

In another exemplary embodiment of the present invention, a computer program or a computer program element is provided that is characterized by being adapted for controlling a device according to one of the above described aspects, which, when being executed by a processing unit, is adapted to perform corresponding method steps.

The computer program element might therefore be stored on a computer unit, which might also be part of an embodiment of the present invention. This computing unit may be adapted to perform or induce a performing of steps of methods associated with the above described devices. Moreover, it may be adapted to operate the components of the above described device. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that exemplary embodiments of the invention are described with reference to different subject matters. In particular, some exemplary embodiments are described with reference to method type claims whereas other embodiments are described with reference to the apparatus type claims.

It has to be noted that exemplary embodiments of the invention are described with reference to different subject matters. In particular, some exemplary embodiments are described with reference to apparatus type claims whereas other exemplary embodiments are described with reference to method type claims. However, a person skilled in the art will gather from the above and the following description that, unless otherwise notified, in addition to any combination of features belonging to one type of subject matter also any combination between features relating to different subject matters, in particular between features of the apparatus type claims and features of the method type claims, is considered to be disclosed with this application. However, all features can be combined providing synergetic effects that are more than the simple summation of the features.

BRIEF DESCRIPTION OF THE DRAWINGS

The aspects defined above and further aspects, features and advantages of the present invention can also be derived from the examples of embodiments to be described herein after and are explained with reference to examples of embodiments, but to which the invention is not limited. The invention will be described in more detail hereinafter with reference to the drawings.

DETAILED DESCRIPTION OF EXEMPLARY EMBODIMENTS

Figure 1:
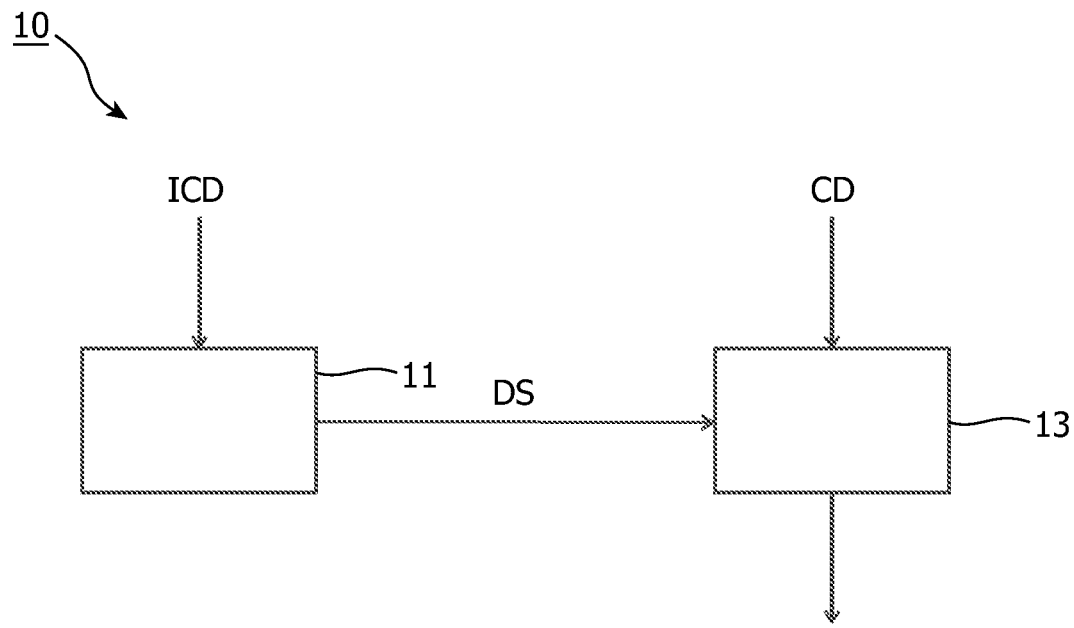
FIG. 1 is a block diagram of a device according to the first embodiment of the invention.

A first exemplary embodiment will be described in the following. FIG. 1 schematically shows a device 10 for automatically identifying a part 20a, 20b of an anatomy structure comprising several parts, in which anatomy structure lies an intervention device 21 according to the first embodiment of the invention. The device 10 comprises a feature extraction unit 11 which is provided with image content data ICD. The feature extraction unit 11 extracts in a step 100 a characterizing feature DS of the appearance of the intervention device 21. The image content data ICD can be provided by an imaging system 30 not shown. The characterizing feature DS of the appearance of the intervention device 21 can be extracted by the feature extraction unit 11 using usual segmentation or image analysis tools.

The device 10 further comprises an anatomy part classification unit 13 which correlates in a step 110 the characterizing feature DS extracted by the feature extraction unit 11 with provided classifier data CD. The classifier data CD can e.g. be provided by a database storing classifier data CD being characteristic for the appearance of intervention device 21 when located in certain anatomy parts 20a, 20b. Thereby, the classifier data CD can e.g. be stored for different angulations of the imaging system 30 and for different locations of the intervention device 21 in the different anatomy parts 20a, 20b. Depending on the result of the correlation between the extracted characterizing feature DS and the classifier data CD the device 10 determines in a step 120 in which part 20a, 20b of the several parts 20a, 20b of the anatomy structure the intervention device 21 is located.

Figure 2:
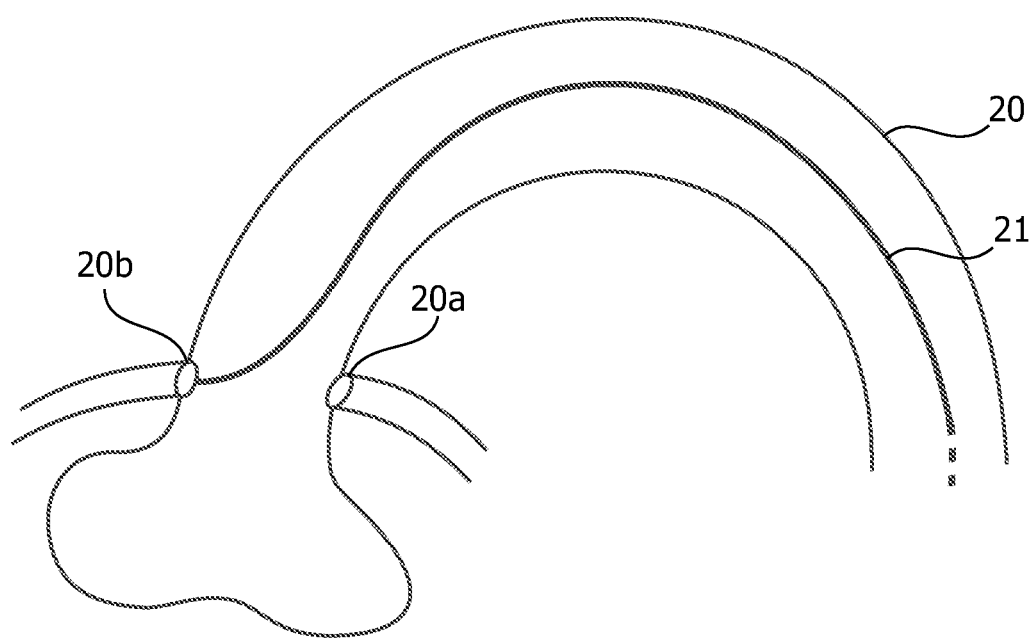
FIG. 2 is a schematic diagram of a vessel structure with an intervention device inside the vessel structure located in a portion of the vessel structure.
Figure 3:
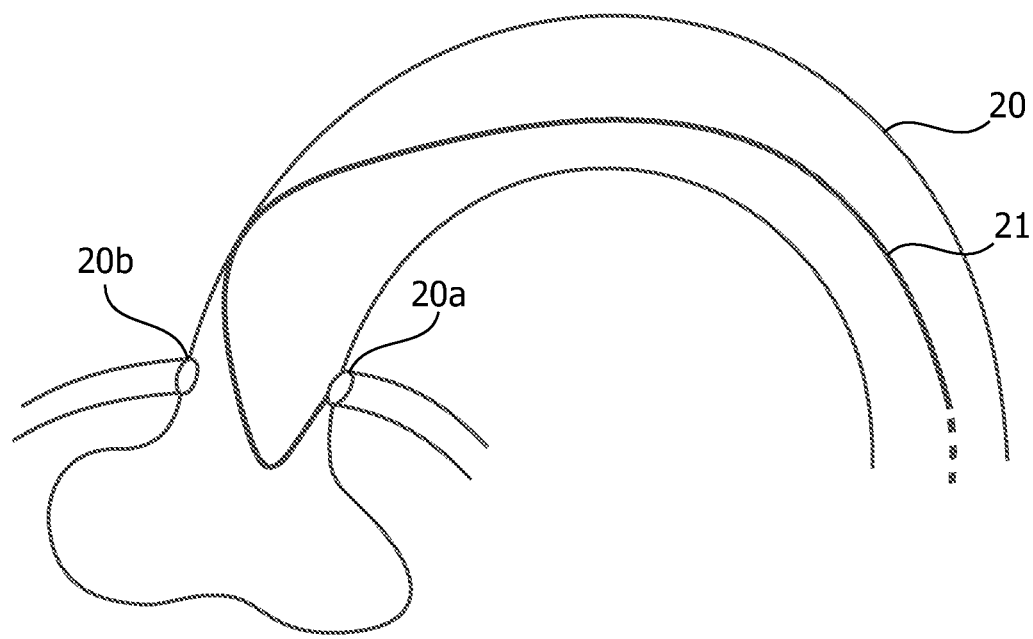
FIG. 3 is a schematic diagram of a vessel structure with an intervention device inside the vessel structure located in another portion of the vessel structure.

FIGS. 2 and 3 are used to exemplarily show how the device 10 automatically identifies an anatomy part 20a, 20b in which an intervention device 21 resides.

FIG. 2 is a schematic diagram of a vessel structure 20 with an intervention device 21 inside the vessel structure 20 located in a portion (part) 20b of the vessel structure 20. In the illustration of FIG. 2 the vessel structure 20 is an aorta 20, the portion 20a, 20b is the left coronary ostium 20a and the right coronary ostium 20b, respectively. In the examples shown in FIGS. 2 and 3 the left 20a and right 20b coronary ostia of the aorta 20 are the anatomy parts 20a, 20b. The intervention device 21 is a catheter 21. The intervention device 21 might also be an electrode, a stent, a balloon which e.g. can be used for expanding a stent, a pacemaker, a guidewire, detachable coils for aneurysm clotting, or any other treatment device. The catheter 21 comprises an injection catheter tip and a catheter body. The diagram in FIG. 2 shows the aortic valve, with the bulgy presence of the sinuses, and above them, the left and right coronary ostia 20a, 20b from which the left and right coronary tree emerge. The aortic cross is a bent structure that will lead to a very different access pattern for the left and right coronaries.

The shape of the aorta 20 and coronary ostia locations 20a, 20b are such that a tool such as the injection catheter tip 21 that enters one of the ostia 20a, 20b does not bend at all in the same way, depending in which ostium 20a, 20b it is entered. It is therefore possible, by examining the device shape DS of this intervention device 21, as seen in a projective image (in this case either from an angiogram or a fluoroscopy sequence), to determine which side of the coronary tree currently is imaged or treated.

In the example of FIG. 2 the catheter 21 is located next to the right coronary ostium 20b. The right coronary ostium 20b can also be entered by the catheter 21. Because the right coronary ostium 20b is situated opposite the aortic cross bending, the access of the catheter 21 can be rather rectilinear with an inflection point.

FIG. 3 shows a similar case as FIG. 2 except that the catheter 21 is located next to the left coronary ostium 20a. The left coronary ostium 20a can also be entered by the catheter 20. FIG. 3 shows how the catheter 21 should be bent in order to reach the left coronary ostium 20a. Because the left coronary ostium 20a is located in a contra-lateral manner to the aortic cross bending, support on the opposite wall (on the right-hand side) should be found before one can enter the left ostium 20a. This typically creates a strong U shape bending at the injection tip.

Therefore, the shape of the catheter 21, and therefore one characterizing feature of the interventional device 21, strongly depends on whether the catheter is located next to or is inserted into the left coronary ostium 20b or the right coronary ostium 20a. That is, the device shape as a characterizing feature DS of the intervention device 21 strongly depends on the location of the device 21 in the vessel structure 20 in relation to a portion 20a, 20b of the vessel structure. It is therefore possible to determine whether the intervention device 21 is located in a portion 20a, 20b of the vessel structure 20 by correlating the extracted device shape being the characterizing featue DS extracted by the feature extraction unit 11 with the provided classifier data CD.

When the anatomy part classification unit 13 determines that the intervention device 21 has the device shape DS shown in FIG. 2 then the device 10 determines in step 120 that the intervention device 21 is located in the portion 20b of the vessel structure 20 and e.g. outputs the information "right". Otherwise, when the anatomy part classification unit 13 determines that the intervention device 21 has the device shape DS shown in FIG. 3 then the device 10 determines in step 120 that the intervention device 21 is located in the portion 20a of the vessel structure 20 and e.g. outputs the information "left".

Therefore, it is possible to identify a part 20a, 20b of the several parts 20a, 20b of the anatomy structure in which the intervention device 21 resides by correlating the extracted characterizing feature DS with the provided classifier data CD.

The step of correlating 110 the extracted characterizing feature DS with the provided classifier data CD conducted by the anatomy part classification unit 13 can be conducted several times. When the correlation is conducted several times with different classifier data CD then the accuracy of the determination in which anatomy part 20a, 20b the intervention device 21 resides can be increased.

In FIG. 2 and FIG. 3 the vessel structure 20 is an aorta. The present invention is also applicable to other vessel structures 20 like e.g. vessel structures in the brain or in other areas of the human and animal body. It can also be applied to other anatomy structures (organs, chambers, cavities).

Furthermore, the imaging system 30 can be an imaging system comprising a source of x-ray radiation 31 and a x-ray detection module 32. The imaging system 30 can also comprise a source of ultrasound 31 and an ultrasound detection module 32. The system geometry of the imaging system 30 is represented by a certain number of parameters such as the field of view, the angulations of the x-ray source 31/ultrasound source 31 and the x-ray detection module 32/ultrasound detection module 32 in relation to the object to be examined.

In order to determine the anatomy part 20a, 20b in which the intervention device 21 resides, e.g. the intervention side, the invention proposes to rely on the presence of an intervention or treatment device 21 in the structure of interest which e.g. might be the vessels 20. The device's appearance like its shape or other characteristics like its radio-opaqueness are analyzed and the corresponding features are extracted. Based on a formal description (model) of the intervention device 21 and of the surrounding anatomy and based on the current system geometry (viewing angle, field of view), the anatomy part classification unit 13 can determine in which anatomy part 20a, 20b, such as the intervention side, the intervention device 21 resides from the entered features. More generally speaking, the anatomy part classification unit 13 can indirectly identify a non-visible anatomy part 20a, 20b from the image data (here the projection) of a visible intervention device 21 residing in this anatomy part 20a, 20b.

Of course the number of anatomy parts 20a, 20b that can be discriminated by the anatomy part classification unit 13 can be more than two. For instance, in the intra-cardiac case, the anatomy part classification unit 13 could determine in which cardiac chamber an ablation catheter is being used. In that case, four distinct parts should be considered (left or right atrium, left or right ventricle).

A second exemplary embodiment will be described in the following. The device 10 according to the second embodiment of the present invention is identical to the device 10 according to the first embodiment of the invention with the exception that the classifier data CD are not stored in a database and are not provided to the device 10 from outside of the device 10 but is generated inside the device 10.

Figure 4:
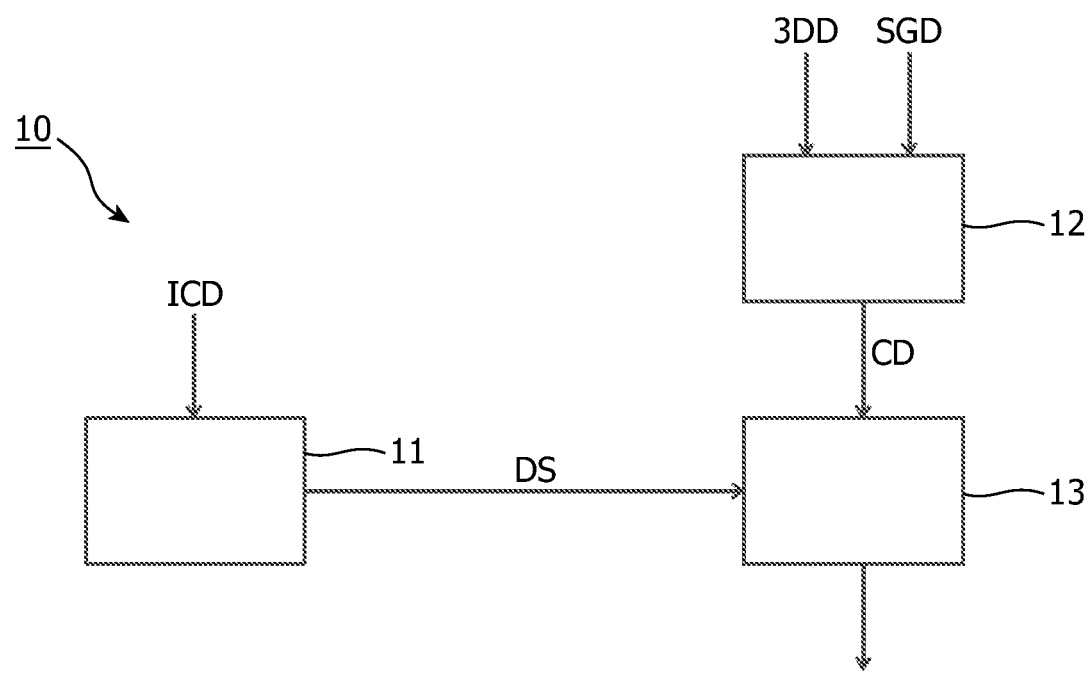
FIG. 4 is a block diagram of a device according to the second embodiment of the invention.

FIG. 4 schematically shows a device 10 for automatically identifying a part 20a, 20b of an anatomy structure comprising several parts 20a, 20b, in which anatomy structure an intervention device 21 resides according to the second embodiment of the invention. The device 10 comprises a feature extraction unit 11 which is provided with image content data ICD. The feature extraction unit 11 extracts in a step 100 a characterizing feature DS of the appearance of the intervention device 21. The image content data ICD can be provided by an imaging system 30 not shown. The characterizing feature DS of the appearance of the intervention device 21 can be extracted by the feature extraction unit 11 using usual segmentation or image analysis tools.

The device 10 further comprises a characterisation unit 12 which generates in a step 130 classifier data CD. The characterisation unit 12 uses three dimensional data 3DD of a model of the intervention device 21 residing in a part 20a, 20b of several parts 20a, 20b of the anatomy structure and uses provided system geometry data SGD of the imaging system 30.

The device 10 further comprises an anatomy part classification unit 13. The anatomy part classification unit 13 is provided with the classifier data CD generated by the characterisation unit 12. The anatomy part classification unit 13 correlates in a step 110 the characterizing feature DS extracted by the feature extraction unit 11 with provided classifier data CD.

When the anatomy part classification unit 13 determines that the intervention device 21 has the characterizing feature DS shown in FIG. 2 then the device 10 determines that the intervention device 21 is located in the anatomy part 20b and e.g. outputs the information "right", i.e. the device 10 identifies the anatomy part 20b in which the intervention device 21 resides. Otherwise, when the anatomy part classification unit 13 determines that the intervention device 21 has the characterizing feature DS shown in FIG. 3 then the device 10 determines that the intervention device 21 is located in the anatomy part 20a and e.g. outputs the information "left", i.e. the device 10 identifies the anatomy part 20a in which the intervention device 21 resides. Of course the number of anatomy parts 20a, 20b that can be discriminated by the anatomy part classification unit 13 can be more than two. For instance, in the intra-cardiac case, the anatomy part classification unit 13 could determine in which cardiac chamber an ablation catheter is being used. In that case, four distinct parts should be considered (left or right atrium, left or right ventricle).

A third exemplary embodiment will be described in the following. The devices 10 according to the third embodiment of the present invention are identical to the devices 10 according to the first and second embodiments of the invention, respectively, with the exception that the feature extraction unit 11 uses further estimated projection characteristics of the appearance of the intervention device 21 residing in an anatomy part 20a, 20b to extract the characterizing feature DS of the appearance of the intervention device 21.

Figure 5:
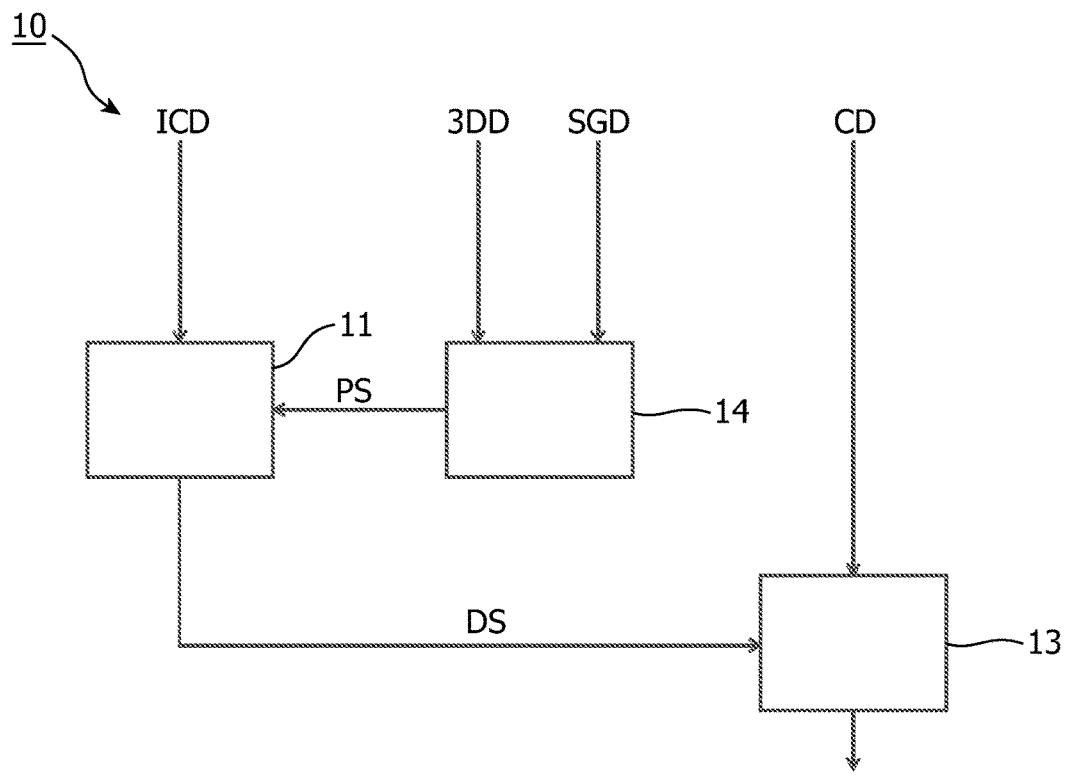
FIGS. 5 and 6 are block diagrams of a device according to the third embodiment of the invention.
Figure 6:
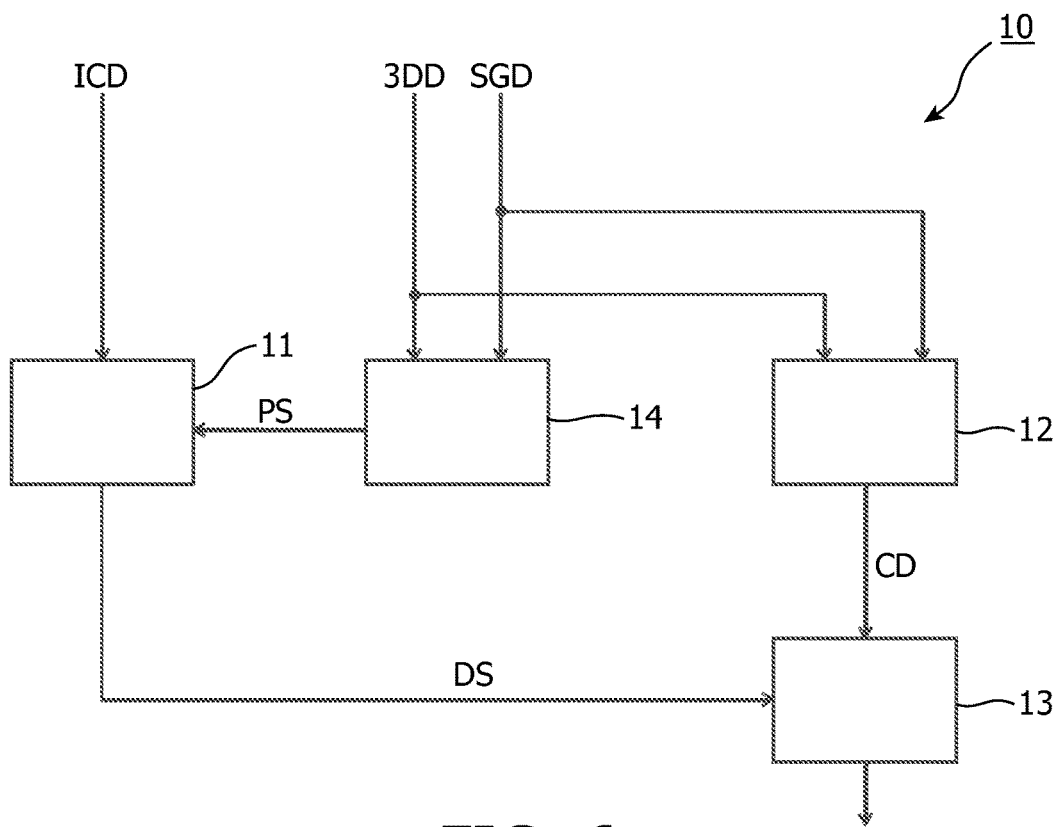

FIGS. 5 and 6 schematically show a device 10 for automatically identifying a part 20a, 20b of an anatomy structure comprising several parts 20a, 20b, in which anatomy structure an intervention device 21 resides according to the third embodiment of the invention. The device 10 comprises a feature extraction unit 11 which is provided with image content data ICD and which receives a projection characteristic PS of the appearance of the intervention device 21 being located in an anatomy part 20a, 20b. The feature extraction unit 11 extracts in a step 100 a characterizing feature DS of the appearance of the intervention device 21. The image content data ICD can be provided by an imaging system 30 not shown. The characterizing feature DS of the appearance of the intervention device 21 can be extracted by the feature extraction unit 11 using usual segmentation or image analysis tools. In this exemplary embodiment, the projection characteristics is meant to help the feature extraction unit 11 focussing on the relevant characterizing feature DS.

The device 10 further comprises an estimation unit 14 which estimates in a step 140 a projection characteristics PS of the appearance of the intervention device 21 being located in a part 20a, 20b of the several parts 20a, 20b of the anatomy structure using provided system geometry data SGD and provided three dimensional data 3DD of a model of the intervention device 21 being located in an anatomy part 20a, 20b. The feature extraction unit 11 uses the estimated projection characteristics PS of the intervention device 21 to extract the characterizing feature DS.

The device 10 further comprises an anatomy part classification unit 13 which correlates in a step 110 the characterizing feature DS extracted by the feature extraction unit 11 with provided classifier data CD. In the device 10 shown in FIG. 5 the classifier data CD can e.g. be provided by a database storing classifier data CD being characteristic for the intervention device 21 located in certain anatomy parts 20a, 20b. Thereby, the classifier data CD can e.g. be stored for different angulations of the imaging system 30 and for different locations 20a, 20b of the intervention device 21. The device 10 shown in FIG. 6 further comprises a characterisation unit 12 which generates in a step 130 the classifier data CD which are provided to the anatomy part classification unit 13. The characterisation unit 12 uses the same three dimensional data 3DD of a model of the intervention device 21 being located in an anatomy part 20a, 20b and uses the same provided system geometry data SGD of the imaging system 30 as the estimation unit 14.

Depending on the result of the correlation between the extracted characterizing feature DS and the classifier data CD the device 10 determines in which part 20a, 20b of the several parts 20a, 20b of the anatomy structure the intervention device 21 resides, i.e. the device 10 identifies an anatomy part 20a, 20b in which the intervention device 21 resides.

When the anatomy part classification unit 13 determines that the intervention device 21 has the characterizing feature DS shown in FIG. 2 then the device 10 determines that the intervention device 21 is located in the anatomy part 20b and e.g. outputs the information "right". Otherwise, when the anatomy part classification unit 13 determines that the intervention device 21 has the characterizing feature DS shown in FIG. 3 then the device 10 determines that the intervention device 21 is located in the anatomy part 20a and e.g. outputs the information "left".

A fourth exemplary embodiment will be described in the following. The device 10 according to the fourth embodiment of the present invention is identical to any one of the devices 10 according to the respective first to third embodiments of the invention with the exception that in the anatomy part classification unit 13 at least one parameter is derived in a step 150 from the extracted characterizing feature DS of the intervention device 21 located in a part 20a, 20b of the several parts 20a, 20b of the anatomy structure. The classifier data CD is at least one classifier parameter CP characteristic for a projection feature of the intervention device 21 located in an anatomy part 20a, 20b. In the step of correlating 110 conducted by the anatomy part classification unit 13 the at least one parameter is correlated with the at least one classifier parameter CP.

The at least one parameter derived from the extracted characterizing feature DS of the intervention device 21 located in an anatomy part 20a, 20b can be e.g. the length of a segment of the intervention device 21, the angle between two segments of the intervention device 21, the radio opaqueness of the interventional device 21 or any other feature of the intervention device 21 which is visible in the image content data ICD obtained by the imaging system 30.

Optionally, the step 110 of correlating conducted by the anatomy part classification unit 13 is conducted more than one time so that more than one parameter respectively derived from the detected characterizing feature DS is correlated with the respective more than one classifier parameter CP. Thereby, the accuracy of the determination in which part 20a, 20b of the several parts 20a, 20b of the anatomy structure the intervention device 21 is located can be increased. More generally speaking the anatomy part classification unit 13 can correlate several features to several characteristics (not necessarily the same number). This means that both the characterizing feature DS and the classifier parameter CP can be seen as set or vector of elementary scalar data. This also applies to the projection characteristics PS.

A fifth exemplary embodiment will be described in the following. The device 10 according to the fifth embodiment is identical to the device 10 according to the fourth embodiment with the exception that in step 150 of deriving the at least one classifier parameter CP a three dimensional model of the aortic cross, the aortic root, the right coronary ostium and the left coronary ostium are used to generate the at least one classifier parameter CP.

Figure 11:
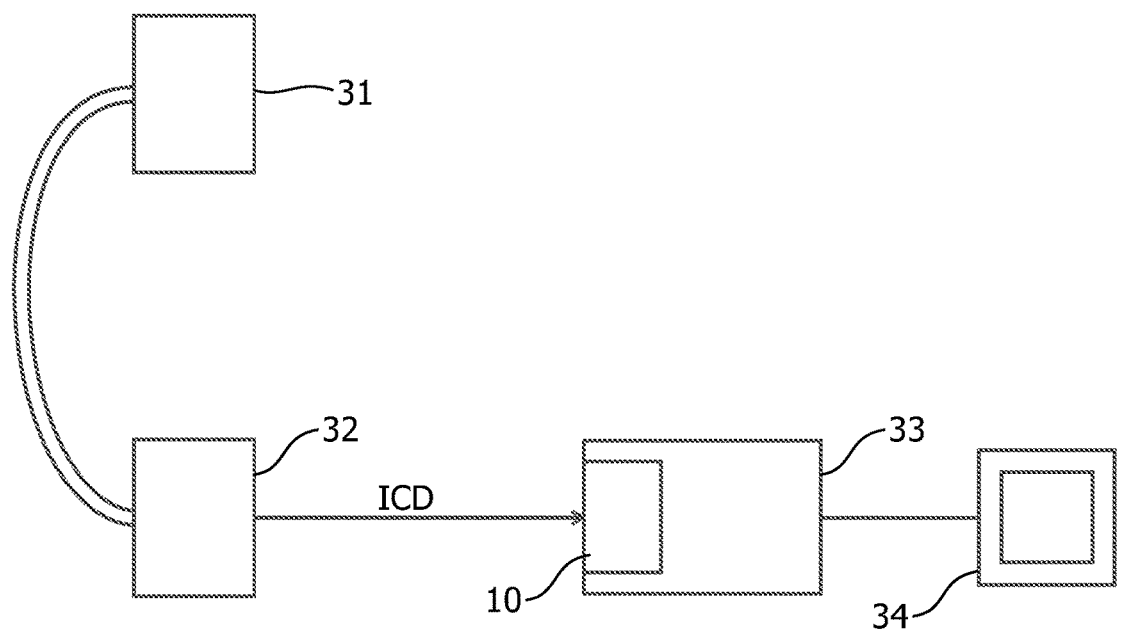
FIG. 11 is a block diagram of an imaging system according to the present invention.

An exemplary embodiment of an imaging system will be described in the following. FIG. 11 is a block diagram of an imaging system 30 according to the present invention. The imaging system 30 comprises a radiation source 31, a radiation detection module 32, a data processing unit 33 with a central processing unit, a memory and a device 10 according to one of the first to fifth embodiment of the present invention. The imaging system 30 further comprises a display unit 34 which is connected with the data processing unit 33. The device 10 receives image content data ICD from the radiation detection module 32.

In FIG. 11 the radiation source 31 and the radiation detection module 32 are part of a C-arm and the radiation source 31 is a x-ray source and the radiation detection module is a x-ray detection module. The invention is not limited thereto. The radiation source 31 and the radiation detection module 32 can also be part of a computer tomography system rotating around an object or subject to be examined.

The imaging system 30 e.g. can be used for percutaneous transluminal coronary angioplasty.

Furthermore, the radiation source 31 can be an ultrasound source 31 and the radiation detection module 32 can be an ultrasound detection module 32. Ultrasounds emitted by the ultrasound source 31 are reflected by the object or subject to be examined and are detected by the ultrasound detection module 32.

Figure 7:
FIG. 7 shows a real fluoroscopic image corresponding to an access in the right coronary tree. The view also shows typical wedge positions to be used in that case.

FIG. 7 shows a real fluoroscopic image obtained with the above described imaging system 30. FIG. 7 corresponds to an access of the intervention device 21 in the right coronary ostium 20b. In FIG. 7 the typical rectilinear shape of the intervention device 21 can be observed. The view also contains typical wedge positions to be used in that case.

Figure 8:
FIG. 8 depicts the same situation as shown in FIG. 7, but in an angio image where the actual right coronary tree can be observed.

FIG. 8 depicts the same situation, but in an angio image where the actual right coronary tree can be observed.

Figure 9:
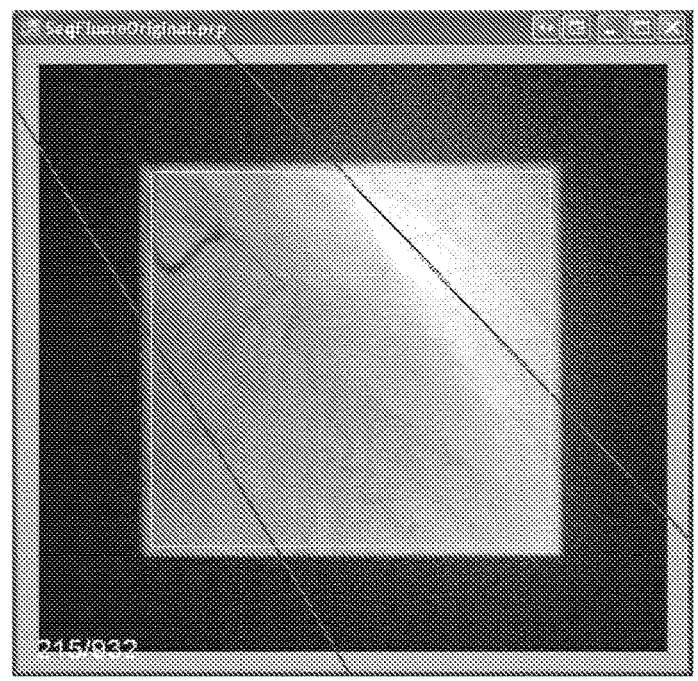
FIG. 9 shows a real fluoroscopic image corresponding to an access in the left coronary tree. The view also shows typical wedge positions to be used in that case.

FIG. 9 shows a real fluoroscopic image obtained with the above described imaging system 30. FIG. 9 corresponds to an access of the intervention device 21 in the left coronary ostium 20a. The U-shape bending of the catheter can clearly be observed. The view also contains typical wedge positions to be used in that case.

Figure 10:
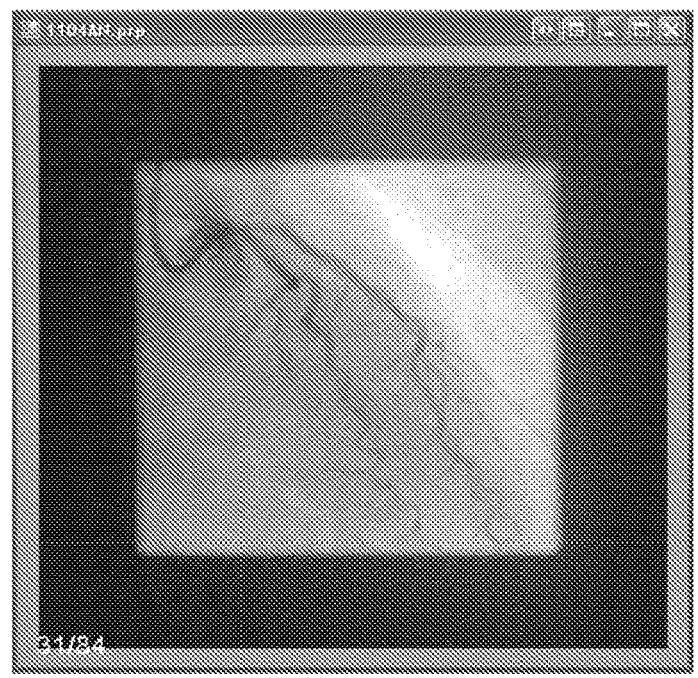
FIG. 10 depicts the same situation as shown in FIG. 9, but in an angio image where the actual left coronary tree can be observed.

FIG. 10 depicts the same situation, but in an angio image where the actual left coronary tree can be observed, with its typical branches (left main, left descending, diagonal, and circumflex).

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage.

A computer program may be stored and/or distributed on a suitable medium, such as an optical storage medium or a solid state medium supplied together with or as part of other hardware, but may also be distributed in other forms, such as via the internet or other wired or wireless telecommunication systems.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

Any reference signs in the claims should not be construed as limiting the scope.

The invention claimed is:

1. A system configured for automatically identifying an anatomy part of an anatomy structure comprising two or more anatomy parts, in which anatomy structure an intervention device resides, the system comprising:
    an imaging system for imaging the anatomy structure using radiation and deriving image content data from the imaging; and
    a processor programmed to:
        extract at least one characterizing feature of an appearance of the intervention device using the derived image content data;
        correlate the at least one characterizing feature with provided classifier data that is linked correspondingly to particular anatomical categories into which said parts would be placeable in classifying said parts; and determine, based on said linked anatomical categories, in which part, from among said two or more anatomy parts, the intervention device is located during an interventional procedure.

2. The system according to claim 1, wherein the processor is further programmed to estimate projection characteristics of the appearance of the intervention device being located in a part from among said two or more anatomy parts of the anatomy structure using provided system geometry data and provided three dimensional data of a model of the intervention device being located in a part from among said two or more anatomy parts of the anatomy structure;

wherein the estimated projection characteristics of the appearance of the intervention device are used to extract the at least one characterizing feature.

3. The system according to claim 1, wherein the intervention device is a catheter, and the part from among said two or more anatomy parts of the anatomy structure is a left coronary ostium or a right coronary ostium of an aorta.

4. The system according to claim 1, further comprising:
a display unit connected with the processor for displaying at least a portion of the image content data.

5. The system of claim 1, wherein said categories include heart structures comprising a left atrium, a right atrium, a left ventricle and a right ventricle.

6. The system of claim 1, wherein said categories include an intervention side of said anatomy structure.

7. The system of claim 1, said two or more parts amounting to more than two.

8. The system of claim 1, said determining entailing selecting from among alternative, said alternative respectively representing ones of said parts.

9. A system for automatically identifying a part of an anatomy structure comprising two or more parts, in which anatomy structure an intervention device resides, the system comprising:
an imaging system for imaging the anatomy structure and deriving image content data from the imaging; and
a processor programmed to:
extract at least one characterizing feature of an appearance of the intervention device using the derived image content data;
correlate the at least one characterizing feature with provided classifier data and to determine in which part, from among the two or more parts, the intervention device is located during an interventional procedure; and
generate classifier data using provided three dimensional data of a model of the intervention device being located in a part of the two or more parts of the anatomy structure and using provided system geometry data of the imaging system.

10. The system of claim 9, said model linking a hypothetical predetermined location of said intervention device with respect to said parts to a respective observable shape of said intervention device.

11. The system of claim 9, said model linking a hypothetical predetermined location of said intervention device with respect to said parts to a respective observable radioopaqueness of said device.

12. The system of claim 9, said two or more parts amounting to more than two.

13. A method for automatically identifying a part of an anatomy structure comprising two or more parts, in which anatomy structure an intervention device resides during an interventional procedure, the method comprising:

imaging the anatomy structure, including an appearance of the intervention device residing in the anatomy structure, to provide image content data;
extracting a characterizing feature of the appearance of the intervention device using the provided image content data;
correlating the extracted characterizing feature with provided classifier data;
determining in which part of the two or more parts of the anatomy structure the intervention device is located during the interventional procedure; and
providing the classifier data using provided three dimensional data of a model of the intervention device being located in a part of the two or more parts of the anatomy structure and using provided system geometry data of an imaging system.

14. The method according to claim 13, further comprising estimating projection characteristics of the intervention device being located in a part of the two or more parts of the anatomy structure using provided system geometry data and provided three dimensional data of a model of the intervention device being located in a part of the two or more parts of the anatomy structure; wherein projection characteristics of the appearance of the intervention device are estimated to produce estimated projection characteristics that are used to perform the extracting of the characterizing feature of the intervention device.

15. The method according to claim 14, further comprising deriving at least one parameter from the extracted characterizing feature of the intervention device located in a part of the two or more parts of the anatomy structure; wherein the classifier data is at least one classifier parameter characteristic for a projection feature of the intervention device located in a part of the two or more parts of the anatomy structure.

16. The method according to claim 15, wherein in deriving the at least one parameter, a three dimensional model of the aortic cross, the aortic root, the right coronary ostium and the left coronary ostium are used to generate the at least one classifier parameter.

17. The method according to claim 13, wherein it is determined that the intervention device is located in a part of the two or more parts of the anatomy structure when the extracted characterizing feature is in a predetermined range of the classifier data.

18. The method according to claim 13, wherein the intervention device is a catheter; and the part of the two or more parts of the anatomy structure is a left coronary ostium or a right coronary ostium of an aorta.

19. The method of claim 13, said two or more parts amounting to more than two.

20. A non-transitory computer readable medium for automatically identifying an anatomy part of an anatomy structure comprising two or more anatomy parts, in which anatomy structure an intervention device resides during an interventional procedure, said medium embodying a program having instructions executable by a processor for performing a method comprising:
causing said anatomy structure to be interrogated using radiation;
based on a result of the interrogating, deriving image content data;
extracting a characterizing feature from the derived image content data of an appearance of the intervention device;
correlating the extracted characterizing feature with provided classifier data; and determining in which anatomy part of the two or more anatomy parts of the anatomy structure the intervention device is located during the interventional procedure, said classifier data comprising a characteristic representative of a depiction of said device, said characteristic being, with respect to said anatomy structure, particular to the determined anatomy part.

21. The computer readable medium of claim 20, said determining being based on a result of said correlating.

22. The computer readable medium of claim 20, said characteristic being indicative of a situation in which said intervention device is located within said determined part.

23. The computer readable medium of claim 20, said depiction, of which said characteristic is representative, being of said device exclusive of surrounding anatomy.

24. The computer readable medium of claim 20, said classifier data including as said characteristic at least one of a shape of said device, a radio-opaqueness of said device, a length of a segment of said device, and an angle between two segments of said device.

25. The computer readable medium of claim 20, said two or more parts amounting to more than two.

26. The computer readable medium of claim 20, said classifier data being linked correspondingly to particular anatomy categories into which said parts would be placeable in classifying said parts, said determining being performed with the links already having been created.

* * * * *